(12) United States Patent
Madriaga et al.

(10) Patent No.: US 7,526,354 B2
(45) Date of Patent: *Apr. 28, 2009

(54) MANAGING AND USING METROLOGY DATA FOR PROCESS AND EQUIPMENT CONTROL

(75) Inventors: Manuel Madriaga, San Jose, CA (US); Junwei Bao, Palo Alto, CA (US); Vi Vuong, Fremont, CA (US)

(73) Assignee: Tokyo Electron Limited, Tokyo (JP)

( * ) Notice: Subject to any disclaimer, the term of this patent is extended or adjusted under 35 U.S.C. 154(b) by 300 days.

This patent is subject to a terminal disclaimer.

(21) Appl. No.: 11/484,484

(22) Filed: Jul. 10, 2006

(65) Prior Publication Data

US 2008/0009081 A1 Jan. 10, 2008

(51) Int. Cl.
*G06F 19/00* (2006.01)

(52) U.S. Cl. .......................... 700/98; 702/81
(58) Field of Classification Search ............. 700/97–98, 700/103, 117–121, 13; 356/625, 636, 237.5, 356/2; 702/81, 82, 117, 155–159, 166, 167; 438/5, 7, 9, 14, 16; 716/1, 4, 19–21
See application file for complete search history.

(56) References Cited

U.S. PATENT DOCUMENTS

| | | |
|---|---|---|
| 5,347,356 A | 9/1994 | Ota et al. |
| 5,468,580 A | 11/1995 | Tanaka |
| 5,926,690 A | 7/1999 | Toprac et al. |
| 6,304,999 B1 | 10/2001 | Toprac et al. |
| 6,383,824 B1 | 5/2002 | Lensing |
| 6,383,888 B1 | 5/2002 | Stirton |
| 6,433,871 B1 | 8/2002 | Lensing et al. |
| 6,451,621 B1 | 9/2002 | Rangarajan et al. |
| 6,597,463 B1 | 7/2003 | Singh et al. |
| 6,609,086 B1 | 8/2003 | Bao et al. |
| 6,625,512 B1 | 9/2003 | Goodwin |
| 6,633,831 B2 | 10/2003 | Nikoonahad et al. |
| 6,643,557 B1 | 11/2003 | Miller et al. |
| 6,657,736 B1 | 12/2003 | Finarov et al. |
| 6,701,206 B1 | 3/2004 | Markle et al. |
| 6,708,075 B2 | 3/2004 | Sonderman et al. |

(Continued)

OTHER PUBLICATIONS http://www.semiconductor.net/article/CA213802.html.*

(Continued)

*Primary Examiner*—Kidest Bahta
(74) *Attorney, Agent, or Firm*—Morrison & Foerster LLP

(57) ABSTRACT

A system for examining a patterned structure formed on a semiconductor wafer using an optical metrology model includes a first fabrication cluster, a metrology cluster, an optical metrology model optimizer, and a real time profile estimator. The first fabrication cluster configured to process a wafer, the wafer having a first patterned and a first unpatterned structure. The first patterned structure has underlying film thicknesses, critical dimension, and profile. The metrology cluster including one or more optical metrology devices coupled to the first fabrication cluster. The metrology cluster is configured to measure diffraction signals off the first patterned and the first unpatterned structure. The metrology model optimizer is configured to optimize an optical metrology model of the first patterned structure using one or more measured diffraction signals off the first patterned structure and with floating profile parameters, material refraction parameters, and metrology device parameters.

31 Claims, 10 Drawing Sheets

U.S. PATENT DOCUMENTS

| | | | |
|---|---|---|---|
| 6,756,243 | B2 | 6/2004 | Pasadyn et al. |
| 6,772,084 | B2 | 8/2004 | Bischoff et al. |
| 6,782,337 | B2 | 8/2004 | Wack et al. |
| 6,785,638 | B2 | 8/2004 | Niu et al. |
| 6,791,679 | B2 * | 9/2004 | Engelhard et al. ............ 356/124 |
| 6,891,626 | B2 | 5/2005 | Niu et al. |
| 6,895,295 | B1 | 5/2005 | Grover et al. |
| 6,943,900 | B2 | 9/2005 | Niu et al. |
| 6,999,254 | B1 | 2/2006 | Phan et al. |
| 7,042,569 | B2 | 5/2006 | Sezginer et al. |
| 7,043,397 | B2 | 5/2006 | Johnson |
| 7,065,423 | B2 | 6/2006 | Prager et al. |
| 7,092,110 | B2 * | 8/2006 | Balasubramanian et al. 356/625 |
| 7,126,700 | B2 * | 10/2006 | Bao et al. .................... 356/625 |
| 7,158,896 | B1 | 1/2007 | Singh et al. |
| 7,186,650 | B1 | 3/2007 | Dakshina-Murthy |
| 7,224,456 | B1 | 5/2007 | Phan et al. |
| 7,224,471 | B2 | 5/2007 | Bischoff et al. |
| 7,280,230 | B2 | 10/2007 | Shchegrov et al. |
| 2004/0017574 | A1 | 1/2004 | Vuong et al. |
| 2004/0150838 | A1 * | 8/2004 | Niu et al. .................... 356/625 |
| 2004/0267397 | A1 | 12/2004 | Doddi et al. |
| 2005/0209816 | A1 | 9/2005 | Vuong et al. |
| 2006/0064280 | A1 | 3/2006 | Vuong et al. |
| 2007/0185684 | A1 | 8/2007 | Vuong et al. |
| 2008/0007739 | A1 | 1/2008 | Vuong et al. |

OTHER PUBLICATIONS

MacCormack et al., Powerful, diffraction-limited semiconductor laser using photorefractive beam coupling, Feb. 15, 1997, Dept. of Physics, University of Southern California, vol. 22, No. 4, pp. 227-229.*

John R McNeil, Scatterometry Applied to Microelectronics Processing, Univ. of New Mexico, IEEE, 2000, p. 37-38.*

Haykin, S. (1999). *Neural Networks*. 2nd edition, M. Horton ed., Prentice Hall: Upper Saddle River, New Jersey, 9 pages (Table of Contents).

Adler, C. L. et al. (Jun. 1997). "High-Order Interior Caustics Produced in Scattering of a Diagonally Incident Plane Wave by a Circular Cylinder," *Journal of the Optical Society of America A* 14(6):1305-1315.

Arthur, G. G. et al. (1997). "Enhancing the Development Rate Model for Optimum Simulation Capability in the Subhalf-Micron Regime," *Proceedings of SPIE* 3049:189-200.

Ausschnitt, C. P. (Feb. 23, 2004). "A New Approach to Pattern Metrology," *Proceedings of SPIE* 5375:51-65.

Benincasa, D. S. et al. P. (Apr. 1987). "Spatial Distribution of the Internal and Near-Field Intensities of Large Cylindrical and Spherical Scatterers," *Applied Optics* 26(7):1348-1356.

Keeman, V. (2005). "Support Vector Machine—An Introduction" In *Support Vector Machines: Theory and Applications*. Wang, L. ed., Springer-Verlag Berlin Heidelberg: The Netherlands, pp. 1-47.

Li, L. (1996). "Formulation and comparison of two recursive matrix algorithms for modeling layered diffraction gratings," *Journal of the Optical Society of America A* 13:1024-1035.

Lock, J. A. et al. (Oct. 2000). "Exterior Caustics Produced in Scattering of a Diagonally Incident Plane Wave by a Circular Cylinder: Semiclassical Scattering Theory Analysis," *Journal of the Optical Society of American A* 17(10):1846-1856.

Owen, J. F. et al. (Nov. 1981). "Internal Electric Field Distributions of a Dielectric Cylinder at Resonance Wavelengths," *Optics Letters* 6(11):540-542.

Platt, J. C. (1999). "Fast Training of Support Vector Machines Using Sequential Minimal Optimization" Chapter 12 In *Advances in Kernel Methods: Support Vector Learning*. Schölkopf et al. eds., MIT Press: Cambridge, MA, pp. 185-208.

U.S. Appl. No. 11/371,752, filed Mar. 8, 2006 for Vuong et al.

U.S. Appl. No. 11/594,659, filed Nov. 7, 2006 for Vuong et al.

U.S. Appl. No. 11/726,076, filed Mar. 20, 2007 for Vuong et al.

U.S. Appl. No. 11/729,700, filed Mar. 28, 2007 for Bischoff et al.

U.S. Appl. No. 11/787,025, filed Apr. 12, 2007 for Jin et al.

Xu. Y. (Jul. 1995). "Electromagnetic Scattering by an Aggregate of Spheres," *Applied Optics* 34(21):4573-4588.

* cited by examiner

MANAGING AND USING METROLOGY DATA FOR PROCESS AND EQUIPMENT CONTROL

BACKGROUND

1. Field

The present application generally relates to optical metrology of a structure formed on a semiconductor wafer, and, more particularly, to optical metrology of patterned structures.

2. Related Art

In semiconductor manufacturing, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured-diffraction signal) is compared to a library of simulated-diffraction signals. Each simulated-diffraction signal in the library is associated with a hypothetical profile. When a match is made between the measured-diffraction signal and one of the simulated-diffraction signals in the library, the hypothetical profile associated with the simulated-diffraction signal is presumed to represent the actual profile of the periodic grating.

The library of simulated-diffraction signals can be generated using a rigorous method, such as rigorous coupled wave analysis (RCWA). More particularly, in the diffraction modeling technique, a simulated-diffraction signal is calculated based, in part, on solving Maxwell's equations. Calculating the simulated diffraction signal involves performing a large number of complex calculations, which can be time consuming and costly.

SUMMARY

An apparatus to examine a patterned structure formed on a semiconductor wafer using an optical metrology model includes a first fabrication system and a metrology processor. The first fabrication system includes a first fabrication cluster, a first metrology cluster, a first metrology model optimizer, and a first real time profile estimator. The first fabrication cluster is configured to process wafers, the wafers having a first patterned and a first unpatterned structures, the first patterned structures having underlying film thicknesses, critical dimension, and profile. The first metrology cluster includes one or more optical metrology devices coupled to the first fabrication cluster. The first metrology cluster is configured to measure diffraction signals off the first patterned and the first unpatterned structures. The first metrology model optimizer is coupled to the first fabrication cluster and the first metrology cluster. The first metrology model optimizer is configured to optimize an optical metrology model of the first patterned structure using one or more measured diffraction signals off the first patterned structure and with floating profile parameters, material refraction parameters, and metrology device parameters. The first real time profile estimator is coupled to the first optical model optimizer and the first metrology cluster. The first real time profile estimator is configured to use the optimized optical metrology model from the first metrology model optimizer, the measured diffraction signals off the first patterned structure, and a fixed value within the range of values for at least one parameter from amongst the material refraction parameters and the metrology device parameters. The first real time profile estimator is configured to create an output comprising underlying film thickness, critical dimension, and profile of the first patterned structure. The metrology processor is coupled to the first fabrication system. The metrology data processor is configured to receive, process, store, and transmit the fixed value within the range of values for the at least one parameter from amongst the material refraction parameters and the metrology device parameters.

DETAILED DESCRIPTION OF EXEMPLARY EMBODIMENT(S)

In order to facilitate the description of the present invention, a semiconductor wafer may be utilized to illustrate an application of the concept. The methods and processes equally apply to other work pieces that have repeating structures. Furthermore, in this application, the term structure when it is not qualified refers to a patterned structure.

Figure 1A:
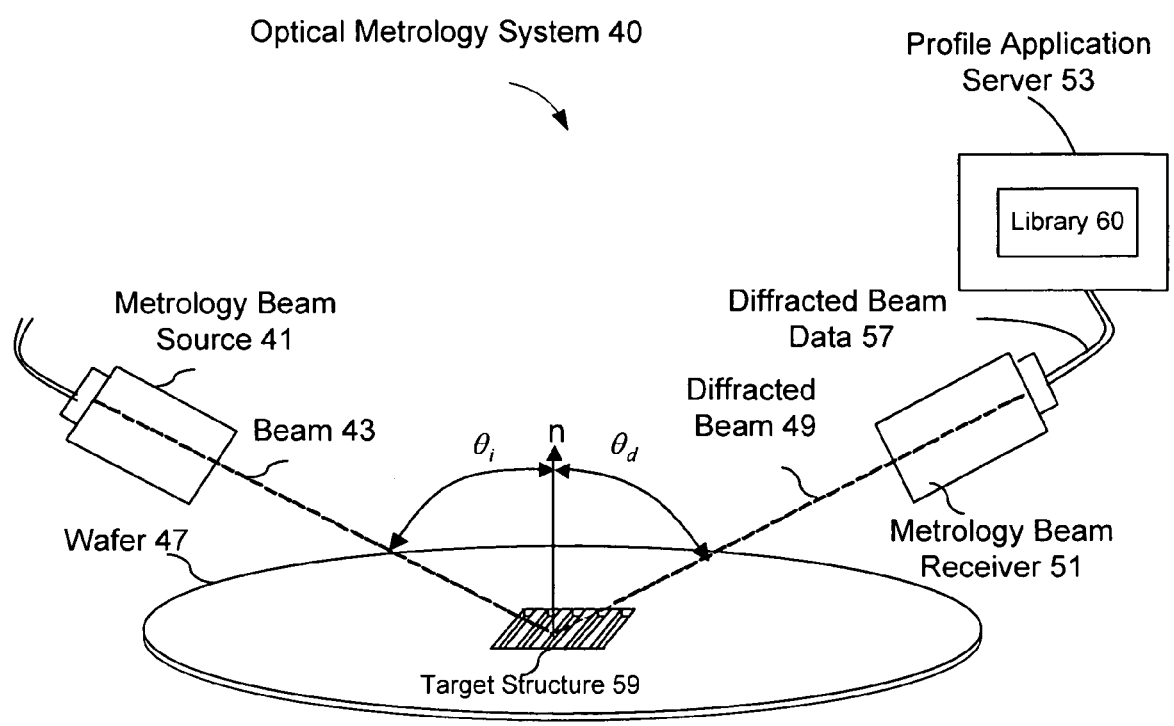
FIG. 1A is an architectural diagram illustrating an exemplary embodiment where optical metrology can be utilized to determine the profiles of structures on a semiconductor wafer.

FIG. 1A is an architectural diagram illustrating an exemplary embodiment where optical metrology can be utilized to determine the profiles of structures on a semiconductor wafer. The optical metrology system 40 includes a metrology beam source 41 projecting a beam 43 at the target structure 59 of a wafer 47. The metrology beam 43 is projected at an incidence angle $\theta_i$ towards the target structure 59, and diffracts at a diffraction angle $\theta_d$. The diffraction beam 49 is measured by a metrology beam receiver 51. The diffraction beam data 57 is transmitted to a profile application server 53. The profile application server 53 compares the measured diffraction beam data 57 against a library 60 of simulated diffraction beam data representing varying combinations of critical dimensions of the target structure and resolution. In one exemplary embodiment, the library 60 instance best matching the measured diffraction beam data 57 is selected. It is understood that although a library of diffraction spectra or signals and associated hypothetical profiles is frequently used to illustrate concepts and principles, the present invention equally applies to a data space comprising simulated diffraction signals and associated set of profile parameters, such as in regression, neural net, and similar methods used for profile extraction. The hypothetical profile and associated critical dimensions of the selected library 60 instance is assumed to correspond to the actual cross-sectional profile and critical dimensions of the features of the target structure 59. The optical metrology system 40 may utilize a reflectometer, an ellipsometer, or other optical metrology device to measure the diffraction beam or signal. An optical metrology system is described in U.S. Pat. No. 6,943,900, entitled GENERATION OF A LIBRARY OF PERIODIC GRATING DIFFRACTION SIGNAL, by Niu, et al., issued on Sep. 13, 2005, and is incorporated in its entirety herein by reference. Other exemplary embodiments of the present invention in optical metrology not requiring the use of libraries are discussed below.

An alternative is to generate the library of simulated-diffraction signals using a machine learning system (MLS). Prior to generating the library of simulated-diffraction signals, the MLS is trained using known input and output data. In one exemplary embodiment, simulated diffraction signals can be generated using a machine learning system (MLS) employing a machine learning algorithm, such as back-propagation, radial basis function, support vector, kernel regression, and the like. For a more detailed description of machine learning systems and algorithms, see "Neural Networks" by Simon Haykin, Prentice Hall, 1999, which is incorporated herein by reference in its entirety. See also U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

Figure 1B:
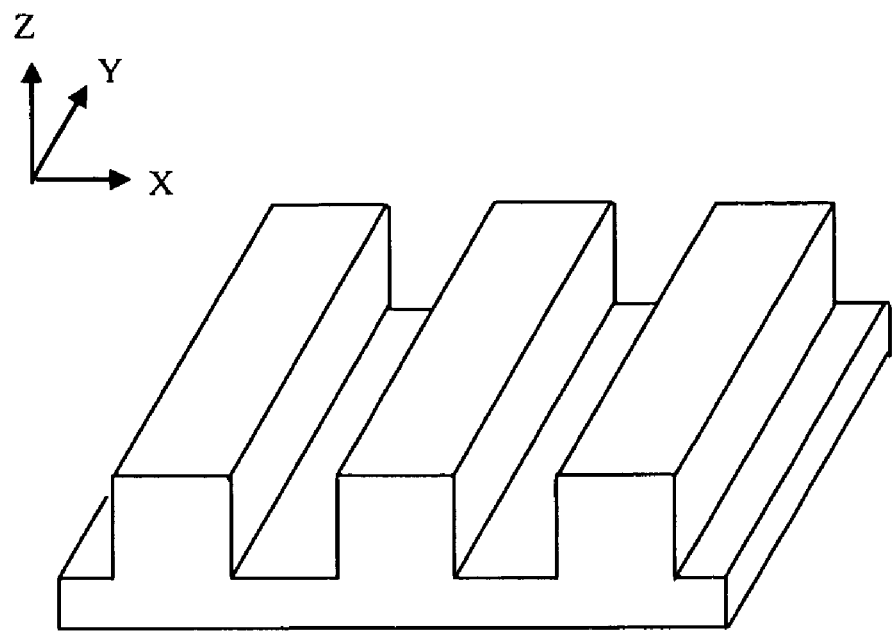
FIG. 1B depicts an exemplary one-dimension repeating structure.

The term "one-dimension structure" is used herein to refer to a structure having a profile that varies only in one dimension. For example, FIG. 1B depicts a periodic grating having a profile that varies in one dimension (i.e., the x-direction). The profile of the periodic grating depicted in FIG. 1B varies in the z-direction as a function of the x-direction. However, the profile of the periodic grating depicted in FIG. 1B is assumed to be substantially uniform or continuous in the y-direction.

Figure 1C:
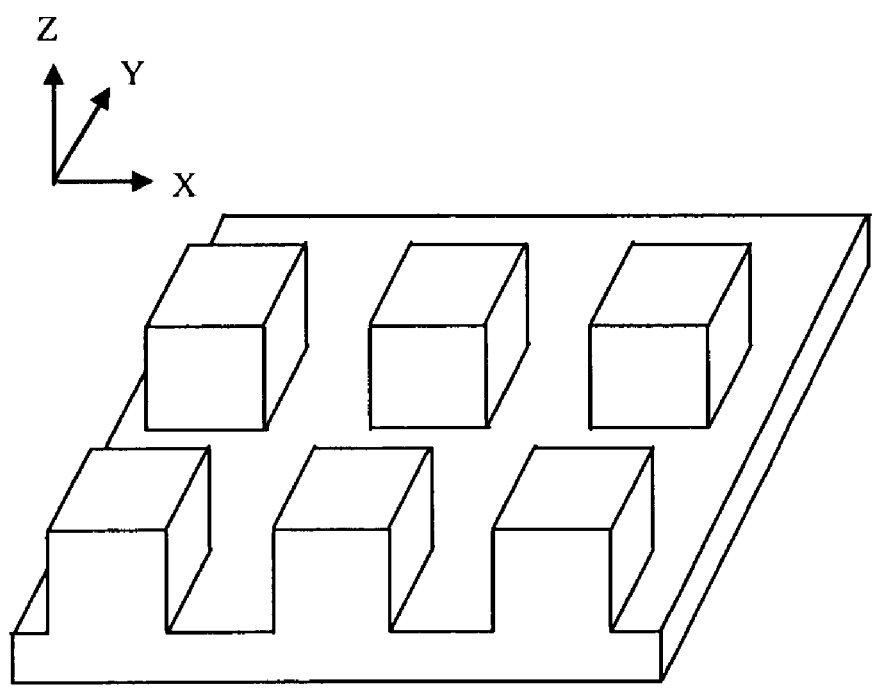
FIG. 1C depicts an exemplary two-dimension repeating structure

The term "two-dimension structure" is used herein to refer to a structure having a profile that varies in at least two-dimensions. For example, FIG. 1C depicts a periodic grating having a profile that varies in two dimensions (i.e., the x-direction and the y-direction). The profile of the periodic grating depicted in FIG. 1C varies in the y-direction.

Figure 2A:
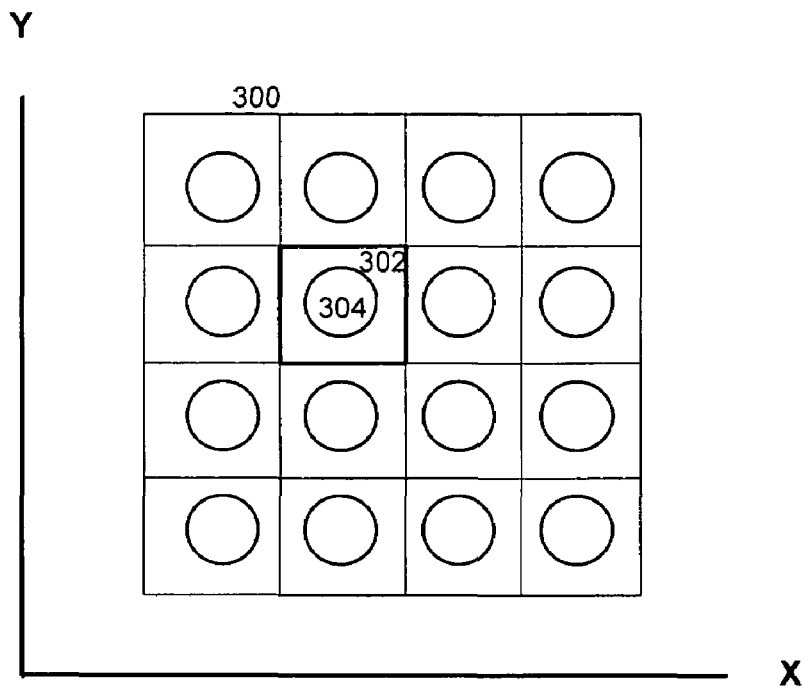
FIG. 2A depicts exemplary orthogonal grid of unit cells of a two-dimension repeating structure.

Discussion for FIGS. 2A, 2B, and 2C below describe the characterization of two-dimension repeating structures for optical metrology modeling. FIG. 2A depicts a top-view of exemplary orthogonal grid of unit cells of a two-dimension repeating structure. A hypothetical grid of lines is superimposed on the top-view of the repeating structure where the lines of the grid are drawn along the direction of periodicity. The hypothetical grid of lines forms areas referred to as unit cells. The unit cells may be arranged in an orthogonal or non-orthogonal configuration. Two-dimension repeating structures may comprise features such as repeating posts, contact holes, vias, islands, or combinations of two or more shapes within a unit cell. Furthermore, the features may have a variety of shapes and may be concave or convex features or a combination of concave and convex features. Referring to FIG. 2A, the repeating structure 300 comprises unit cells with holes arranged in an orthogonal manner. Unit cell 302 includes all the features and components inside the unit cell 302, primarily comprising a hole 304 substantially in the center of the unit cell 302.

Figure 2B:
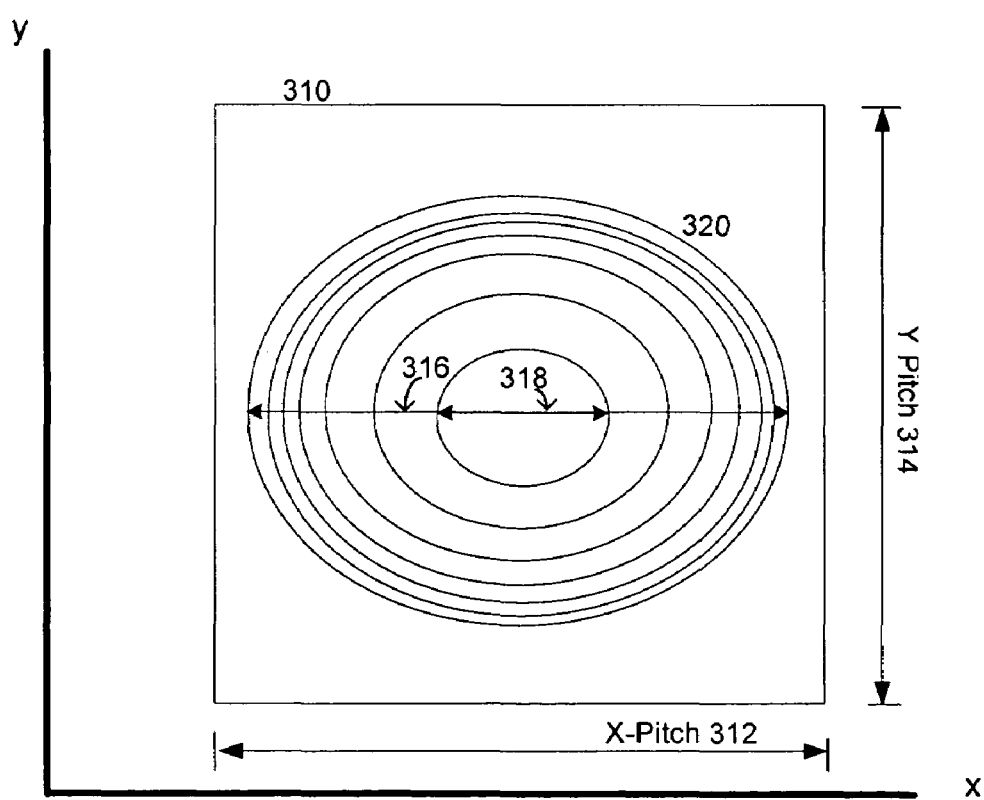
FIG. 2B depicts a top-view of a two-dimension repeating structure.

FIG. 2B depicts a top-view of a two-dimension repeating structure. Unit cell 310 includes a concave elliptical hole. FIG. 2B shows a unit cell 310 with a feature 320 that comprises an elliptical hole wherein the dimensions become progressively smaller until the bottom of the hole. Profile parameters used to characterize the structure includes the X-pitch 312 and the Y-pitch 314. In addition, the major axis of the ellipse 316 that represents the top of the feature 320 and the major axis of the ellipse 318 that represents the bottom of the feature 320 may be used to characterize the feature 320. Furthermore, any intermediate major axis between the top and bottom of the feature may also be used as well as any minor axis of the top, intermediate, or bottom ellipse, (not shown).

Figure 2C:
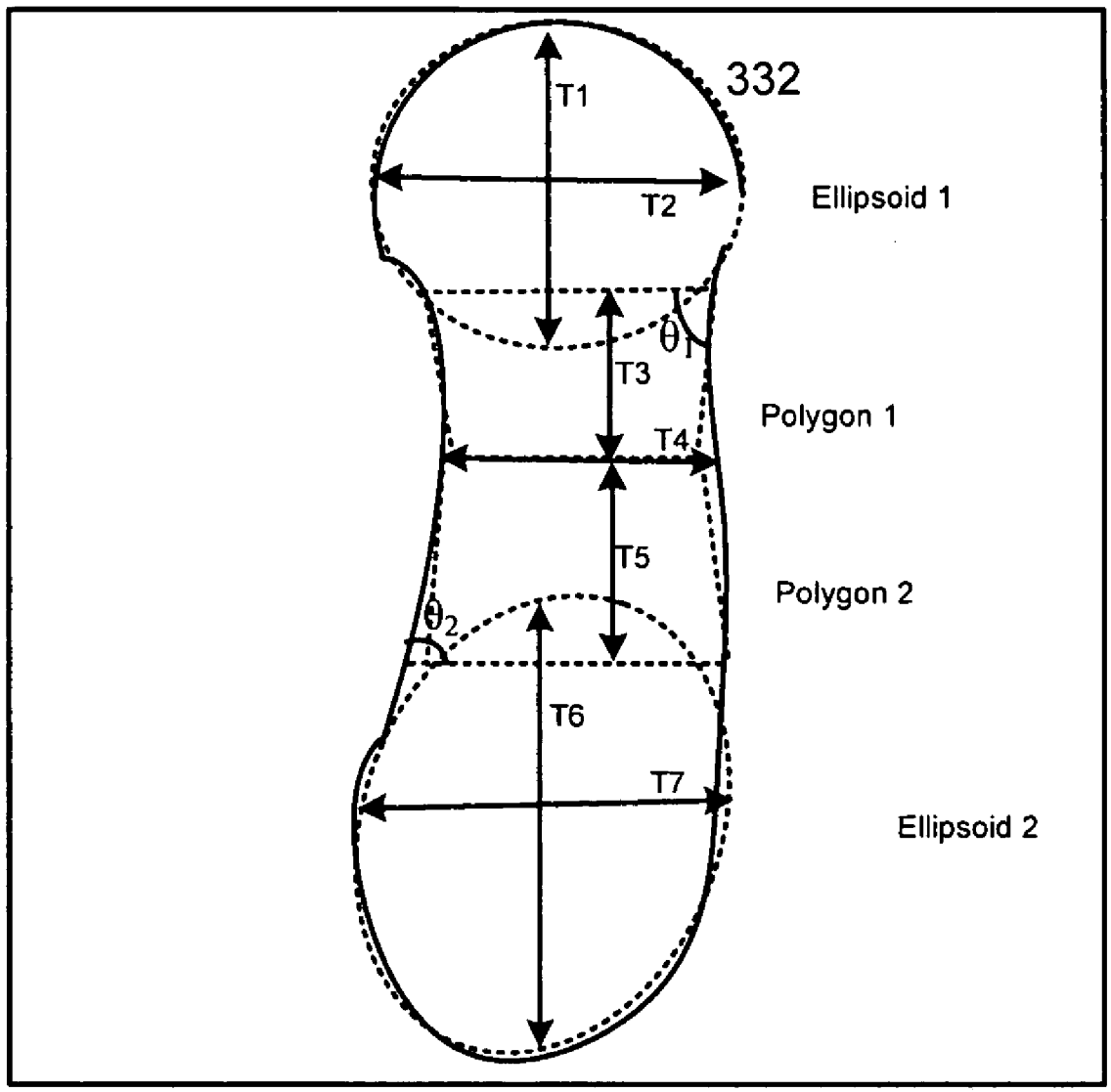
FIG. 2C is an exemplary technique for characterizing the top-view of a two-dimension repeating structure.

FIG. 2C is an exemplary technique for characterizing the top-view of a two-dimension repeating structure. A unit cell 330 of a repeating structure is a feature 332, an island with a peanut-shape viewed from the top. One modeling approach includes approximating the feature 332 with a variable number or combinations of ellipses and polygons. Assume further that after analyzing the variability of the top-view shape of the feature 322, it was determined that two ellipses, Ellipsoid 1 and Ellipsoid 2, and two polygons, Polygon 1 and Polygon 2 were found to fully characterize feature 332. In turn, parameters needed to characterize the two ellipses and two polygons comprise nine parameters as follows: T1 and T2 for Ellipsoid 1; T3, T4, and $\theta_1$ for Polygon 1; T4, T5, and $\theta_2$ for Polygon 2; T6 and T7 for Ellipsoid 2. Many other combinations of shapes could be used to characterize the top-view of the feature 332 in unit cell 330. For a detailed description of modeling two-dimension repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, and is incorporated in its entirety herein by reference.

Figure 3:
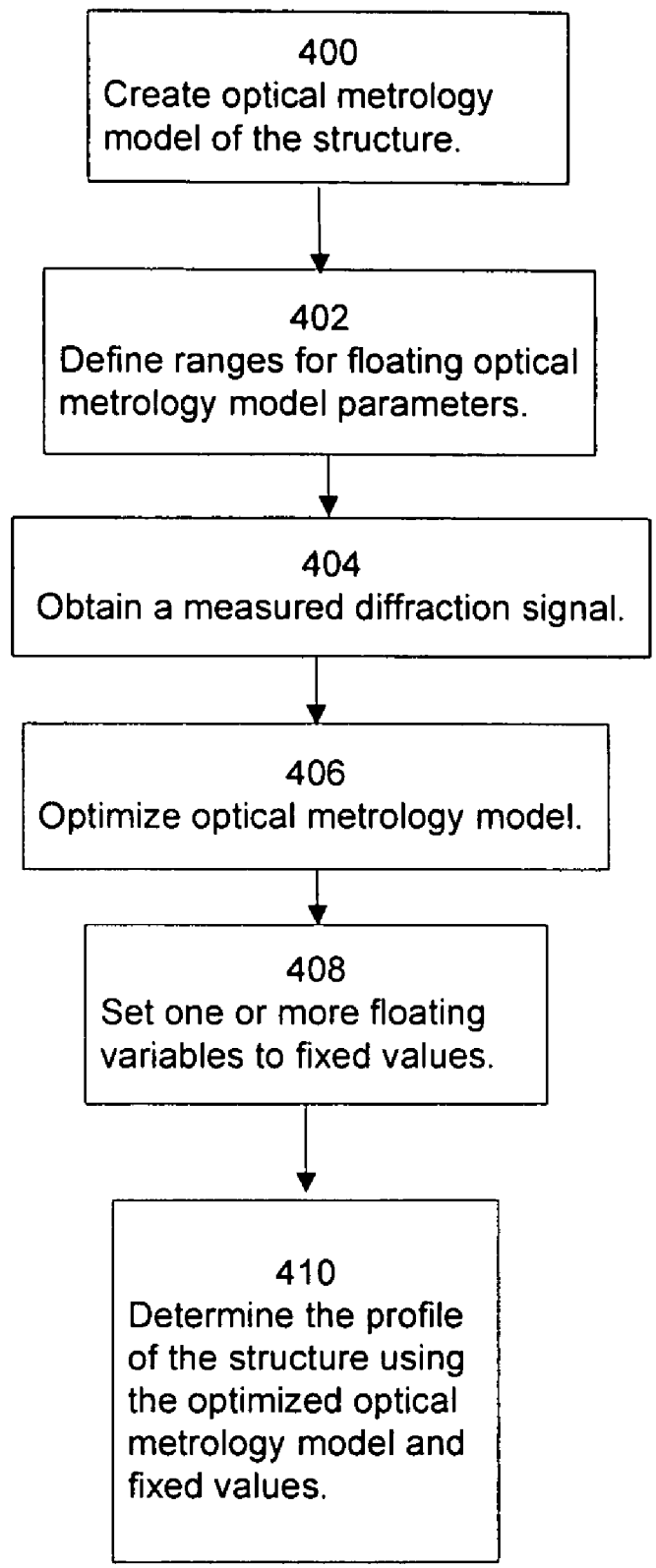
FIG. 3 is an exemplary flowchart for determining profile parameters of wafer structures using obtained values of optical metrology variables.

FIG. 3 is an exemplary flowchart for examining a patterned structure formed on a semiconductor wafer. Referring to FIG. 3, in step 400, an optical metrology model of the patterned structure is created. The optical metrology model includes parameters characterizing the profile of the patterned structure (i.e., profile parameters), parameters related to the material refraction used in the layers of the structure (i.e., material refraction parameters), and parameters related to the metrology device and angular settings of the illumination beam relative to the repeating structure (i.e., metrology device parameters).

As mentioned above, profile parameters can include height, width, sidewall angle, and characterization of profile features, such as top-rounding, T-topping, footing, and the like. Also mentioned above, profile parameters for repeating structures can include X-pitch and Y-pitch of the unit cell, major and minor axes of ellipses and dimensions of polygons used to characterize the top-view shape of hole or island, and the like.

Still referring to FIG. 3, material refraction parameters include the refractive index, N parameter, and the extinction coefficient, K parameter, as represented in the following equations:

$$N(\lambda, a) = a_1 + \frac{a_2}{\lambda^2} + \frac{a_3}{\lambda^4} \qquad 1.1$$

$$K(\lambda, b) = \frac{b_1}{\lambda} + \frac{b_2}{\lambda^3} + \frac{b_3}{\lambda^5} \qquad 1.2$$

$$a = [a_1, a_2, a_3] \qquad 1.3$$

$$b = [b_1, b_2, b_3]. \qquad 1.4$$

where $\lambda$ is the wavelength, a is the refractive index constant for the material, and b is extinction coefficient constant for the material. Instead of floating N and K, the constants a and b can be floated in the optical metrology model.

In step 402, the ranges of profile parameters, material refraction parameters, and metrology device parameters are defined. In one example, ranges of the material refraction parameters (e.g., N and K parameters) and the metrology device parameters (e.g., angle of incidence and azimuth angle of the incident beam relative to the direction of periodicity of the repeating structure) are defined. As noted above, constants a and b can be used for the N and K parameters.

In step 404, a measured diffraction signal is obtained, where the measured diffraction signal was measured off the patterned structure using an optical metrology device. In one example, a particular optical metrology device can be selected and used to obtain the measured diffraction signal. The optical metrology device may be a reflectometer, ellipsometer, hybrid reflectometer/ellipsometer, and the like.

In step 406, the optical metrology model is optimized using the measured diffraction signal and ranges of the profile parameters, material refraction parameters, and metrology device parameters. For example, an initial optical metrology model can be defined. One or more simulated diffraction signals can be generated for the initial optical metrology model using values for the profile parameters, material refraction parameters, and metrology device parameters within the ranges defined in step 402. The one or more simulated diffraction signals can be compared to the measured diffraction signal. The results of this comparison can be evaluated using one or more termination criteria, such as a cost function, goodness of fit (GOF), and the like. If the one or more termination criteria are not met, the initial optical metrology model can then be altered to generate a refined optical metrology model. The process of generating one or more diffraction signals and comparing the one or more diffraction signals to the measured diffraction signal can be repeated. This process of altering the optical metrology model can be repeated until the one or more termination criteria are met to obtain an optimized metrology model. For detailed description of metrology model optimization, refer to U.S. patent application Ser. No. 10/206,491, OPTIMIZED MODEL AND PARAMETER SELECTION FOR OPTICAL METROLOGY, by Vuong, et al., filed Jun. 27, 2002; Ser. No. 10/946,729, OPTICAL METROLOGY MODEL OPTIMIZATION BASED ON GOALS, by Vuong, et al., filed Sep. 21, 2004; and U.S. patent application Ser. No. 11/061,303, OPTICAL METROLOGY OPTIMIZATION FOR REPETITIVE STRUCTURES, by Vuong, et al., filed on Apr. 27, 2004, all of which are incorporated herein by reference in their entireties.

Figure 4A:
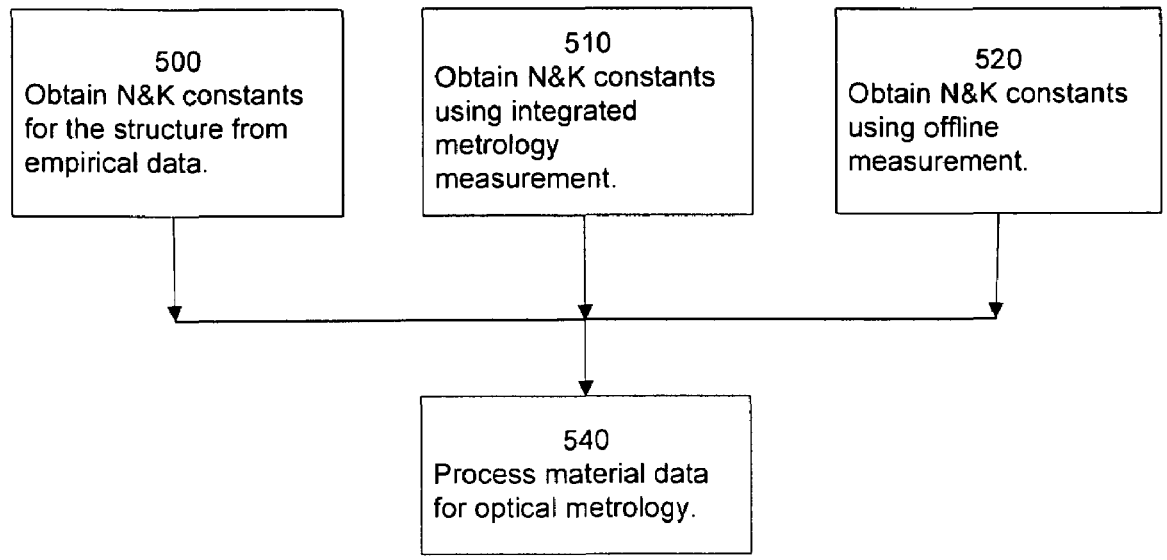
FIG. 4A is an exemplary flowchart of techniques to obtain refraction indices for wafer structures.
Figure 4B:
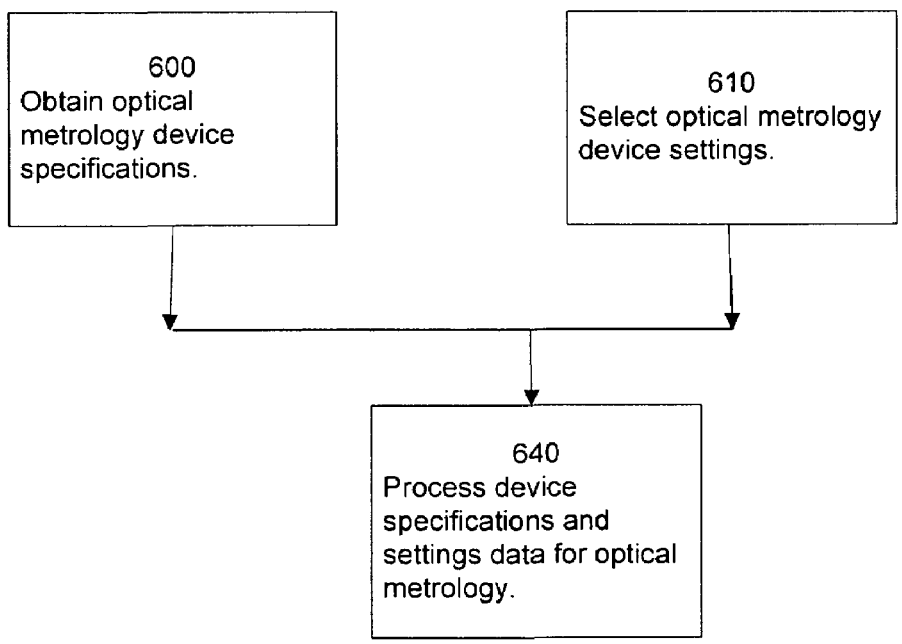
FIG. 4B is an exemplary flowchart for obtaining values for metrology device variables.

In step 408, for at least one parameter from amongst the material refraction parameters, and the metrology device parameters, at least one parameter is set to a fixed value within the range of values for the at least one parameter. FIGS. 4A and 4B are exemplary flowcharts of techniques to obtain values of parameters of the optical metrology model, which can be used as the fixed values in step 408.

FIG. 4A is an exemplary flowchart of techniques to obtain values of the N and K parameters. In step 500, the N and K parameters, including constants a and b, are obtained from empirical data, such as similar data from previous wafer structures using the same materials, historical values of the constants from previous runs of the same recipe and from publications or handbooks. In step 510, the N and K parameters, including constants a and b, are obtained from measurements using the optical metrology device integrated with a fabrication equipment, such as an etch or a track integrated fabrication equipment. In step 520, the N and K parameters, including constants a and b, are obtained using offline optical metrology devices.

In one embodiment, the site measured in step 520 is an unpatterned area adjacent to the patterned structure. In another embodiment, the site measured is not adjacent to the patterned structure and may be in a test area of the same wafer or in an area of a test wafer. In another embodiment, one site is measured per wafer, or per lot and the constants a and b obtained are used for the same wafer, for the whole lot of wafers, or for a whole process run. Alternatively, a previous correlation of the thickness of the layer and the constants a and b may be used to obtain the values of the constants a and b once the thickness of the layer is determined.

Referring to FIG. 4A, in step 540, the material data obtained from various sources and using various techniques are processed for use in the profile determination of the patterned structure. For example, if several measurements are made to determine the constants a and b, a statistical average may be calculated.

FIG. 4B is a flowchart for obtaining values for metrology device parameters. In one embodiment, in step 600, based on a selected metrology device, the angle of incidence of the illumination beam is obtained from the vendor specifications or from the setting used for the application if the metrology device has a variable angle of incidence. Similarly, in step 610, the azimuth angle may be determined based on the selected optical metrology device and the wafer structure application. In step 640, the process device specifications and settings data for optical metrology are processed. Given a reflectometer with normal incidence or an ellipsometer with a fixed angle of incidence as the selected metrology device, the normal incidence or the fixed angle is converted into the format required for the optical metrology model. Similarly, if the azimuth angle of the metrology device is also converted into the format required for the optical metrology model.

Referring to FIG. 3, in step 410, the profile of the patterned structure can be. determined using the optimized optical metrology model and the fixed value in step 408. In particular, at least one profile parameter of the patterned structure is determined using the optimized optical metrology model and the fixed value in step 408. The at least one profile parameter can be determined using a regression process or a library-based process.

As mentioned above, in a regression process, a measured diffraction signal measured off the patterned structure is compared to simulated diffraction signals, which are iteratively generated based on sets of profile parameters, to get a convergence value for the set of profile parameters that generates the closest match simulated diffraction signal compared to the measured diffraction signal. For a more detailed description of a regression-based process, see U.S. Pat. No. 6,785,638, titled METHOD AND SYSTEM OF DYNAMIC LEARNING THROUGH A REGRESSION-BASED LIBRARY GENERATION PROCESS, issued on Aug. 31, 2004, which is incorporated herein by reference in its entirety.

In a library-based process, an optical metrology data store is generated using the optimized metrology model. The optical metrology data store having pairs of simulated diffraction signals and corresponding set of profile parameters. A detailed description of generating optical metrology data such as a library of simulated diffraction signals and corresponding set of profile parameters is described in U.S. Pat. No. 6,943,900, entitled GENERATION OF A LIBRARY OF PERIODIC GRATING DIFFRACTION SIGNAL, by Niu, et al., issued on Sep. 13, 2005, and is incorporated in its entirety herein by reference.

In one embodiment, the profile of the patterned structure is determined using a measured diffraction signal and a subset of the metrology data store that are within the fixed value in step 408. For example, if the a and b constant values of the N and K parameters were fixed in step 408, then the portion of the optical metrology data store used would be the simulated diffraction signals and set of profile parameters corresponding to fixed values of a and b.

In another embodiment, the profile of the patterned structure is determined using a measured diffraction signal and the entire optical metrology data store, i.e., searching the entire data space. For example, the profile of the patterned structure is determined using the measured diffraction signal and the entire metrology data, i.e., floating the a and b constants while searching for the best match simulated diffraction signal.

Figure 5:
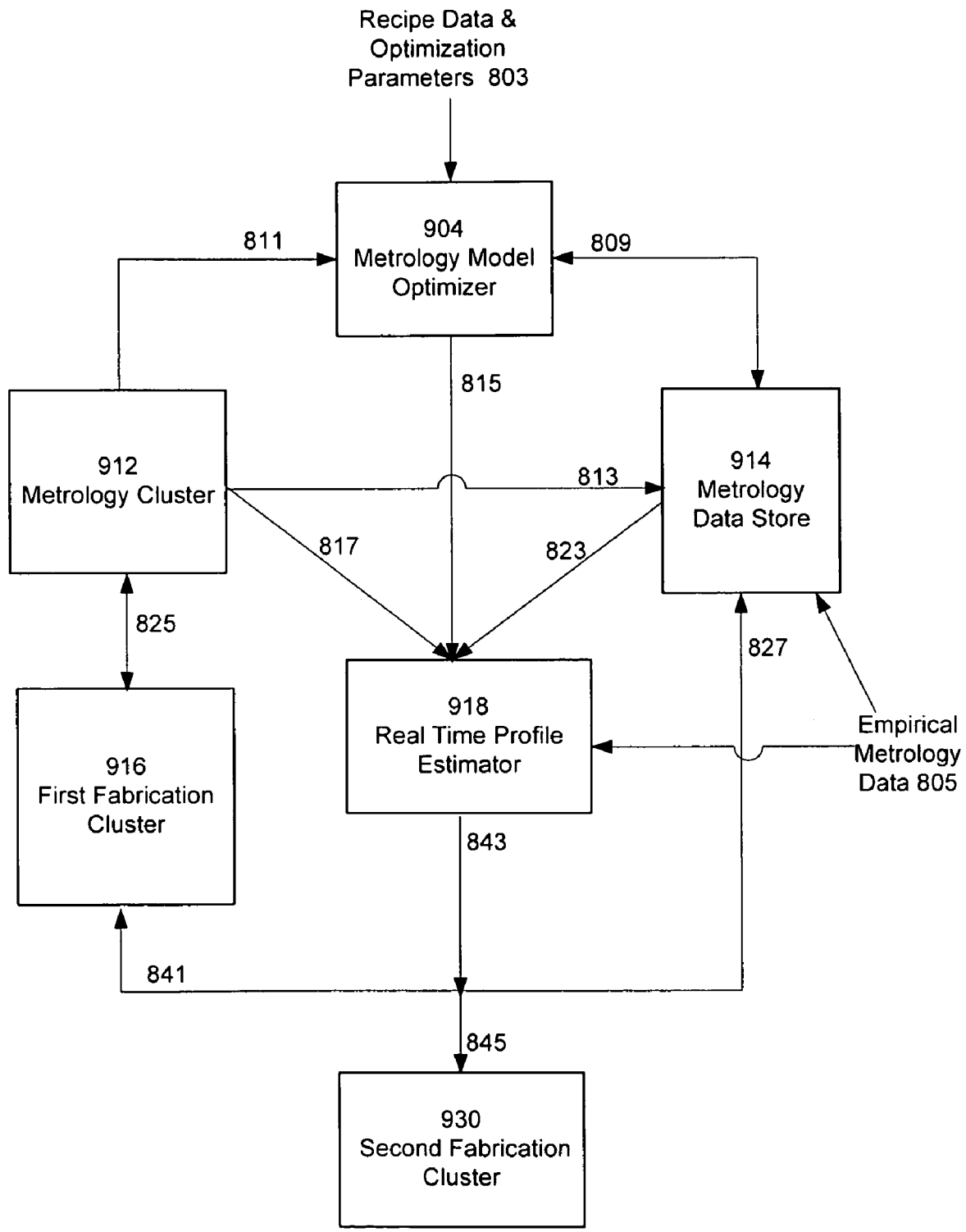
FIG. 5 is an exemplary architectural diagram of an embodiment for a real time profile estimator.

FIG. 5 is an exemplary architectural diagram of a real time profile estimator. A first fabrication cluster 916 is coupled to a metrology cluster 912. The first fabrication cluster 916 may include one or more of a photolithography, etch, thermal processing system, metallization, implant, chemical vapor deposition, chemical mechanical polishing, or other fabrication unit. The first fabrication cluster 916 processes the wafer (not shown) through one or more process step. After each process step, the wafer may be measured in the metrology cluster 912. The metrology cluster 912 may be an inline or offline set of metrology devices such as reflectometers, ellipsometers, hybrid reflectometers/ellipsometers, scanning electron microscopes, sensors, and the like.

After measuring the wafer structure, the metrology cluster 912 transmits diffraction signals 811 to the model optimizer 904. The metrology model optimizer 904 uses the fabrication recipe input information and optimization parameters 803, previous empirical structure profile data 809 from the metrology data store 914 and measured diffraction signals 811 from the metrology cluster 912 to create and optimize an optical metrology model of the structure measured. Recipe data 803 include materials in the layers of the patterned and unpatterned structures in the stack. Optimization parameters 803 include profile parameters, material refraction parameters, and metrology device parameters that are floated in the optical metrology model. The model optimizer 904 optimizes the optical metrology model based on the measured diffraction signals 811 off the patterned structure, the recipe data and optimization parameters 803, empirical data 809 from the metrology data store 914 and creates an optimized optical metrology model 815 transmitted to the real time profile estimator 918.

Referring to FIG. 5, the real time profile estimator 918 uses the optimized optical metrology model 815, measured diffraction signals 817, and empirical metrology data 805 to determine the patterned structure profile, critical dimension, and underlying thicknesses 843. The empirical metrology data 805 may include fixed profile parameters (such as pitch), the N and K parameters (such as constants a and b), and/or metrology device parameters (such as angle of incidence and/or azimuth angle). The output of the real time profile estimator 918 is further selectively transmitted as data 841 to the first fabrication cluster 916, transmitted as data 827 to the metrology data store 914 for storage, and transmitted as data 845 to the second fabrication cluster 930.

Data 841 transmitted to the first fabrication cluster 916 may include an underlying film thicknesses, CD, and/or values of one or more profile parameters of the patterned structure. The underlying film thicknesses, CD, and/or values of one or more profile parameters of the patterned structure may be used by the first fabrication cluster to alter one or more process parameter such as focus and dose for a photolithography fabrication cluster or dopant concentration for an ion implantation fabrication cluster. The data 845 transmitted to the second fabrication cluster 930 may include the patterned structure CD that may be used to alter the etchant concentration in an etch fabrication cluster or the deposition time in a deposition cluster. The data 827 transmitted to the metrology data store comprises underlying film thicknesses, CD, and/or values of the profile parameters of the patterned structure together with identification information such as wafer identification (ID), lot ID, recipe, and patterned structure ID to facilitate retrieval for other applications.

Referring to FIG. 5, as mentioned above, the metrology data store 914 may utilize identification information such as wafer ID, lot ID, recipe, and patterned structure ID as a means for organizing and indexing the metrology data. Data 813 from the metrology cluster 912 includes measured diffraction signals associated with identification for the wafer, lot, recipe, site or wafer location, and patterned structure or unpatterned structure. Data 809 from the metrology model optimizer 904 includes variables associated with patterned structure profile, metrology device type and associated variables, and ranges used for the variables floated in the modeling and values of variables that were fixed in the modeling. As mentioned above, empirical metrology data 805 may include fixed profile parameters (such as pitch), the N and K parameters (such as constants a and b), and/or metrology device parameters (such as angle of incidence and/or azimuth angle).

Figure 6:
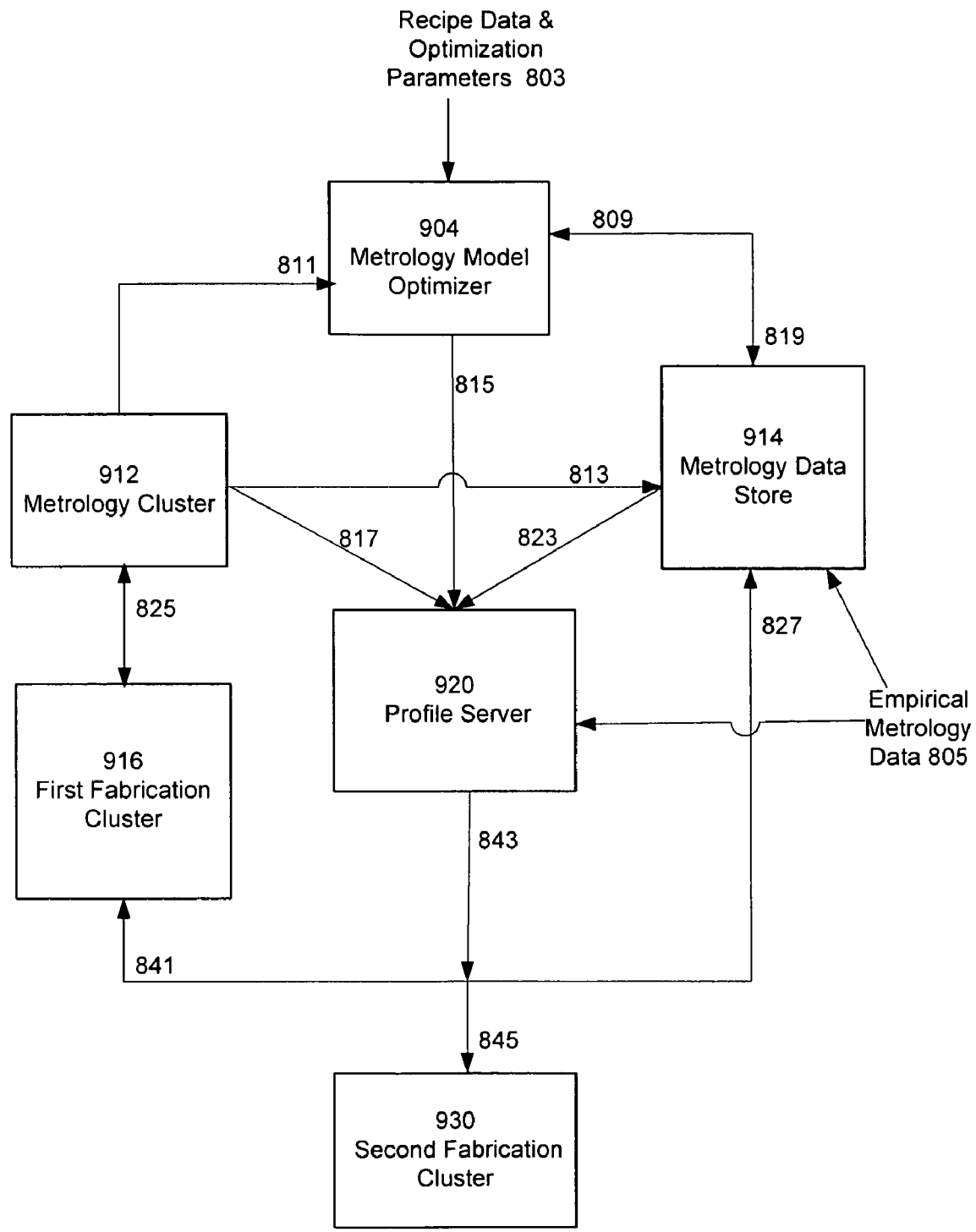
FIG. 6 is an exemplary architectural diagram of an embodiment for creating and using a profile server data store.

FIG. 6 is an exemplary architectural diagram of an embodiment for creating and using a profile server to determine the profile corresponding to a measured diffraction signal. FIG. 6 is similar to FIG. 5 with two exceptions. First, the model optimizer 904 in FIG. 6 may create one of two data sets or both data sets in addition to optimizing the metrology model. The first data set is a library of pairs of simulated diffraction signals and the corresponding set of profile parameters. The second data set is a trained machine learning system (MLS) where the MLS may be trained with a subset of the library, first data set mentioned above. The first and/or the second data set 819 are stored in the metrology data store 914. Secondly, the real time profile estimator 918 in FIG. 5 is replaced by a profile server 920 in FIG. 6. The profile server 920 uses either the library data set or the trained MLS data set that is made available from the metrology model optimizer 904. Alternatively, the profile server 920 may access the stored data sets in the metrology data store 914. The profile server 920 uses the measured diffraction signals 817 from the metrology cluster 912, the library or the trained MLS from the metrology data store 914 to determine the underlying film thicknesses, CD, and profile parameters of the patterned structure 843. In addition, the profile server 920 may use empirical metrology data 805 comprising fixed profile parameters (such as pitch), the N and K parameters (such as constants a and b), and/or metrology device parameters (such as angle of incidence and/or azimuth angle) to set boundaries of the library or trained MLS that is used to find the best match to the measured diffraction signal 817.

Figure 7:
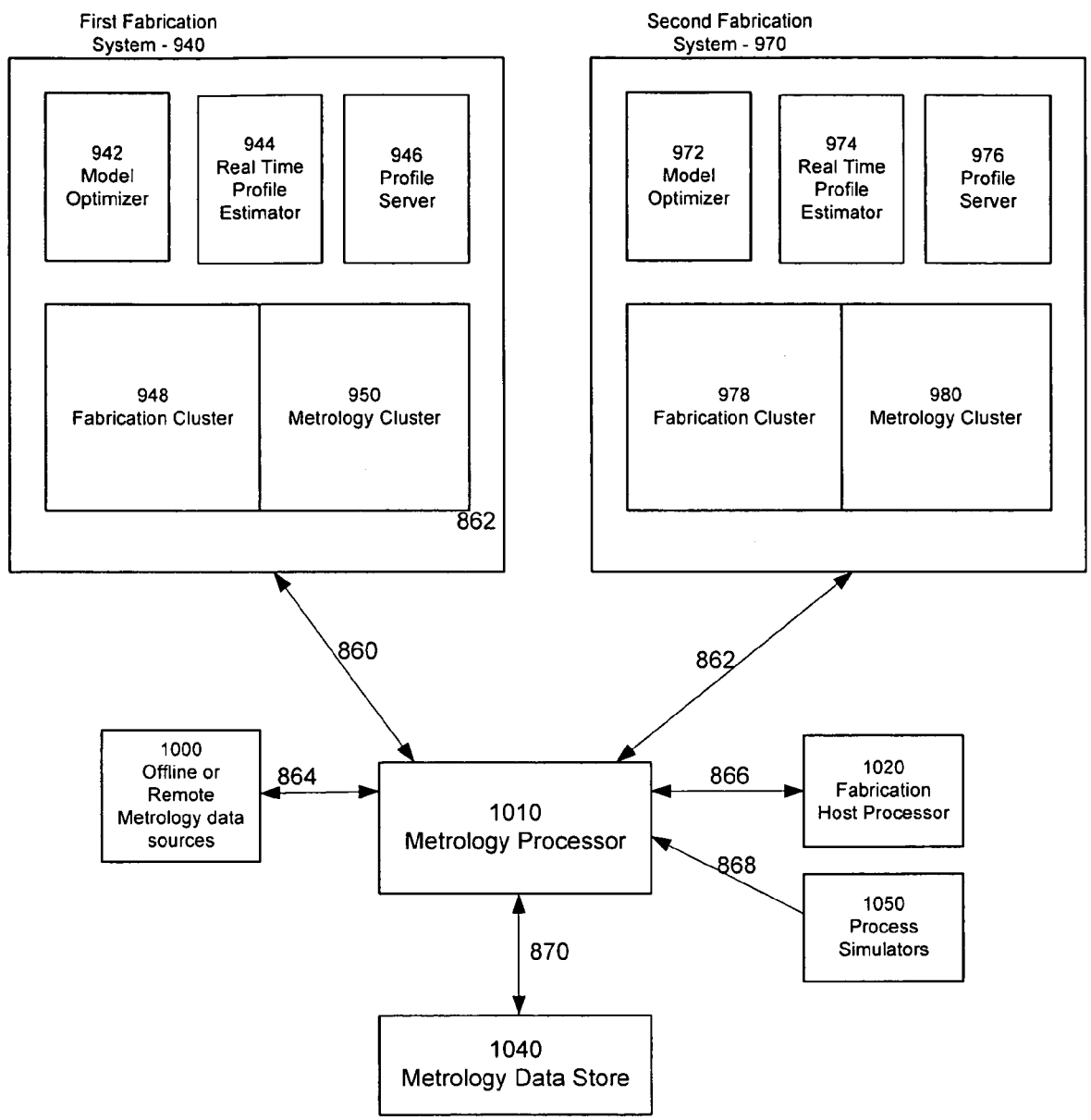
FIG. 7 is an exemplary architectural diagram for linking two or more fabrication systems with a metrology processor and a metrology data store to determine profile parameters of patterned structures.

FIG. 7 is an exemplary architectural diagram for linking two or more fabrication systems with a metrology processor and a metrology data store to determine profile parameters of patterned structures. A first fabrication system 940 includes a model optimizer 942, a real time profile estimator 944, profile server 946, a fabrication cluster 948, and a metrology cluster 950. The first fabrication system 940 is coupled to a metrology processor 1010. The metrology processor 1010 is coupled to metrology data sources 1000, a metrology data store 1040, the fabrication host processors 1020, and to process simulator 1050.

Referring to FIG. 7, the components of the first fabrication system 940, i.e., the model optimizer 942, the real time profile estimator 944, the profile server 946, the fabrication cluster 948, and the metrology cluster 950 are configured respectively to perform functions the same as the corresponding devices described in FIG. 5 and FIG. 6. The metrology processor 1010 receives metrology data 864 from the offline or remote metrology data sources 1000. The offline metrology data sources 1000 may be an offline cluster of metrology devices in the fabrication site such as reflectometers, ellipsometers, SEM's and the like. The remote metrology data sources 1000 may include a remote data server or remote processor or website that provides metrology data for the application. Data 860 from the first fabrication system 940 to the metrology processor 1010 may include the profile parameter ranges of the optimized metrology model and the generated data stores to determine the structure profile parameters. The data stores 1040 may include a library of pairs of simulated diffraction signals and corresponding sets of profile parameters or a trained MLS system that can generate a set of profile parameters for an input measured diffraction signal. Data 870 from data stores 1040 to metrology processor 1010 includes a set of profile parameters and/or simulated diffraction signal. Data 860 from the metrology processor 1010 to the first metrology system 940 includes values of the profile parameters, material refraction parameters, and metrology device parameters in order to specify the portion of the data space to be searched in the library or trained MLS store in the metrology data store 1040. Data 862 transmitted to and from the second fabrication system 970 to the metrology processor 1010 are similar to the data 860 transmitted to and from the first fabrication system 940.

Still referring to FIG. 7, data 866 transmitted to and from the metrology processor 1010 to the fabrication host processor 1020 may include data related to the application recipe and process data measured by the metrology clusters, 950 and 980, in the first and second fabrication systems, 940 and 970. Data 868 such as profile parameter values calculated using process simulators 1050 are transmitted to the metrology processor 1010 for use in setting selected variables of the metrology model to fixed values. Examples of process simulators are Prolith™, Raphael™, Athena™, and the like. Alternatively, the profile parameter values may be used by the profile server 946 and 976 to define the data space to search in the library or trained MLS store in the metrology data store 1040. The metrology data store 1040 in FIG. 7 is the repository of metrology data and the metrology data is made available to the first and/or the second fabrication system, 940 and 970. As mentioned above, the first and/or second fabrication system, 940 and 970, may include one or more of a photolithography, etch, thermal processing system, metallization, implant, chemical vapor deposition, chemical mechanical polishing, or other fabrication unit.

Figure 8:
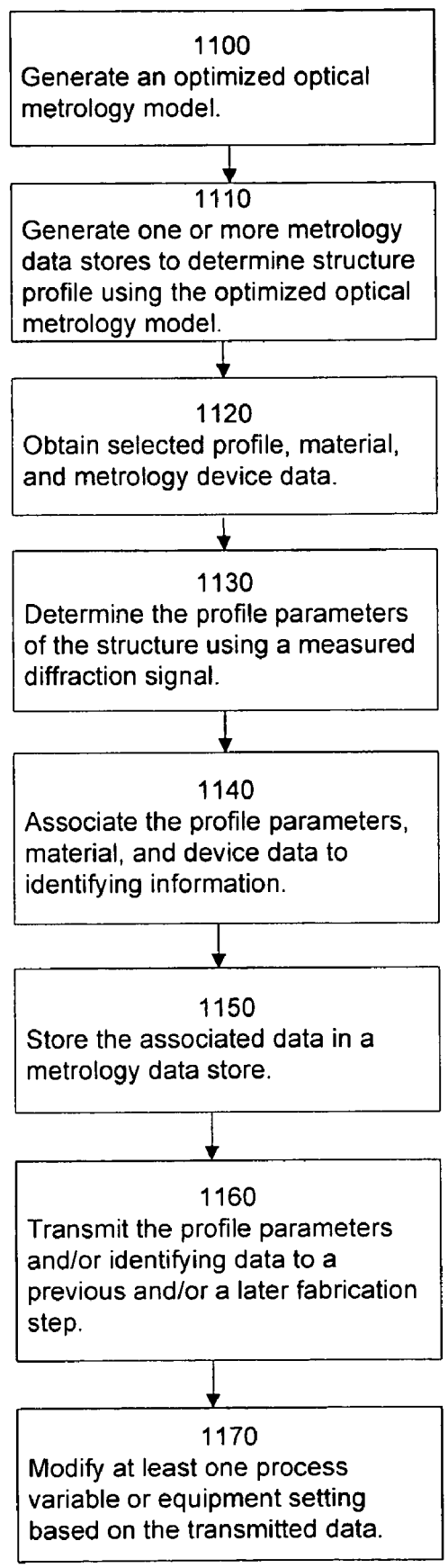
FIG. 8 is an exemplary flowchart for managing and utilizing metrology data for automated process and equipment control.

FIG. 8 is an exemplary flowchart for managing and utilizing metrology data for patterned structure profile determination and automated process and equipment control. In step 1100, an optical metrology model is created and optimized using the method described in FIG. 3. In step 1110, one or more data stores to determine the structure profile parameters are generated using the optimized optical metrology model. The data stores may include a library of pairs of simulated diffraction signals and corresponding sets of profile parameters or a trained MLS system that can generate a set of profile parameters for an input measured diffraction signal. In step 1120, data for profile parameters, material refraction parameters, and metrology device parameters are obtained. As mentioned above, selected profile parameters are those that can be made constant or fixed by using measured values or historical data for a similar wafer application. Values for material refraction parameters are the a and b constants for refractive index N and extinction coefficient K. Values for the metrology device parameters, such as angle of incidence, are obtained from the vendor specifications of the metrology device. Values for azimuth angle are obtained from the setup used in the diffraction measurement. In step 1130, the profile parameters, critical dimension (CD), and underlying thicknesses are determined using a measured diffraction signal.

Referring to FIG. 8, in step 1140, the profile parameters and material data of the structure is associated with identifying information. Identifying information includes site of the measured structure, wafer, wafer lot, run, application recipe, and other fabrication related data. In step 1150, the metrology data and associated identifying information are stored in a metrology data store. The metrology data and/or associated identifying information may be transmitted to a later or a previous fabrication process step, in step 1160. In step 1170, the transmitted metrology data and/or associated identifying information are used to modify at least one process variable of a later or a previous fabrication process step or an equipment control variable in the previous, current or later fabrication process step. For example, a value of the middle critical dimension (MCD) of a structure at an etch process step is transmitted to a previous lithography process step where the value of the MCD is used to modify a dose and/or focus of the stepper in a photolithography process step. Alternatively, a bottom critical dimension (BCD) of a structure may be transmitted to an etch process step and the value of the BCD is used to modify the length of etching or the concentration of the etchant. In another embodiment, the MCD may be sent to a current process, such as a post exposure bake (PEB) process step where the value of the MCD is used to modify the temperature of the PEB process. The MCD may also be used to modify a process variable in the current process, such as the pressure in a reaction chamber in an etch process.

In particular, it is contemplated that functional implementation of the present invention described herein may be implemented equivalently in hardware, software, firmware, and/or other available functional components or building blocks. For example, the metrology data store may be in computer memory or in an actual computer storage device or medium. Other variations and embodiments are possible in light of above teachings, and it is thus intended that the scope of invention not be limited by this Detailed Description, but rather by Claims following.

We claim:

1. An apparatus for examining a patterned structure formed on a semiconductor wafer using an optical metrology model, the system comprising:

a first fabrication system comprising:

a first fabrication cluster configured to process wafers, the wafers having a first patterned and a first unpatterned structures, the first patterned structures having underlying film thicknesses, critical dimension, and profile;

a first metrology cluster including one or more optical metrology devices coupled to the first fabrication cluster, the first metrology cluster configured to measure diffraction signals off the first patterned and the first unpatterned structures;

a first metrology model optimizer coupled to the first fabrication cluster and the first metrology cluster, the first metrology model optimizer configured to optimize an optical metrology model of the first patterned structure using one or more measured diffraction signals off the first patterned structure and with floating profile parameters, material refraction parameters, and metrology device parameters;

a first real time profile estimator coupled to the first optical model optimizer and the first metrology cluster, configured to use the optimized optical metrology model from the first metrology model optimizer, the measured diffraction signals off the first patterned structure, and a fixed value within the range of values for at least one parameter from amongst the material refraction parameters and the metrology device parameters, and wherein the first real time profile estimator is configured to create an output comprising underlying film thickness, critical dimension, and profile of the first patterned structure; and a metrology processor coupled to the first fabrication system, the metrology data processor configured to receive, process, store, and transmit the fixed value within the range of values for the at least one parameter from amongst the material refraction parameters and the metrology device parameters.

2. The apparatus of claim 1 wherein the metrology processor is further configured to receive, process, store, and transmit the optimized optical metrology model, and underlying film thickness, profile parameters, critical dimension, material refractive parameters, and metrology device parameters of the first patterned structure.

3. The apparatus of claim 1 the first fabrication system further comprises:

a first profile server coupled to the first optical model optimizer and the first metrology cluster, configured to use the optimized optical metrology model from the first optical metrology model optimizer, the measured diffraction signals off the first patterned structure, and the fixed value, and wherein the first profile server is configured to create an output comprising underlying film thickness, critical dimension, and profile of the first patterned structure.

4. The apparatus of claim 1 wherein the material refraction parameters including a refractive index (N) parameter and an extinction coefficient (K) parameter.

5. The apparatus of claim 4 wherein the N parameter is represented by a vector a in the expression $N(\lambda, a)$ and the K parameter is represented by b in the expression $K(\lambda, b)$, wherein $\lambda$ is the wavelength.

6. The apparatus of claim 5 wherein the N parameter and K parameter are fixed to an N and K values of layers of the patterned structure measured using the first optical metrology cluster.

7. The apparatus of claim 6 wherein the N and K values of layers of the first patterned structure were measured from the first unpatterned structure or an unpatterned area in the same wafer or an unpatterned area of a test wafer.

8. The apparatus of claim 7 wherein at least 2 sites on a wafer are measured and a statistical average is calculated.

9. The apparatus of claim 5 wherein the N parameter and K parameter are fixed to empirical or theoretical N and K values for the same material.

10. The apparatus of claim 9 wherein the metrology device parameters include angle of incidence and/or azimuth angle.

11. The apparatus of claim 1 further comprising
a metrology data store coupled to the metrology data processor, the metrology data store configured to store and access the optimized optical metrology model and the fixed value of the first patterned structure.

12. The apparatus of claim 11 wherein the metrology data store is configured to store and access pairs of simulated diffraction signals and corresponding sets of profile parameters for the first patterned structure.

13. The apparatus of claim 11 wherein the metrology data store is configured to store and access sets of training data for an optical metrology machine language system and/or a trained optical metrology machine language system for the first patterned structure.

14. The apparatus of claim 11 wherein the metrology data processor is coupled to a second fabrication system.

15. The apparatus of claim 14 wherein the second fabrication system is configured to process the wafer, the wafer having a second patterned and a second unpatterned structure, the second patterned structure having underlying film thicknesses, critical dimension, and profile, the second fabrication system comprising:

a second fabrication cluster configured to process wafers, the wafers having a second patterned and a second unpatterned structures, the first patterned structures having underlying film thicknesses, critical dimension, and profile;

a second metrology cluster including one or more optical metrology devices coupled to the second fabrication cluster, the second metrology cluster configured to measure diffraction signals off the second patterned and the second unpatterned structure;

a second metrology model optimizer coupled to the second fabrication cluster and the second metrology cluster, the second metrology model optimizer configured to optimize a second optical metrology model of the second patterned structure using one or more measured diffraction signals off the second patterned structure and with floating profile parameters, material refraction parameters, and metrology device parameters;

a second real time profile estimator coupled to the second optical model optimizer and the second metrology cluster, configured to use the optimized optical metrology model from the second metrology model optimizer, the measured diffraction signals off the second patterned structure, and a fixed value with the range of values for at least one parameter from amongst the material refraction parameters and the metrology device parameters, and wherein the second real-time profile estimator is configured to create an output comprising underlying film thickness, critical dimension, and profile of the second patterned structure.

16. The apparatus of claim 15 the second fabrication system further comprises:

a second profile server coupled to the second optical model optimizer and the second metrology cluster, configured to use the optimized optical metrology model from the second optical metrology model optimizer, the measured diffraction signals off the second patterned structure, and the fixed value, and configured to create an output comprising underlying film thickness, critical dimension, and profile of the second patterned structure.

17. The apparatus of claim 16 wherein at least one of the underlying film thickness, critical dimension, and profile of the first patterned structure is used to alter at least one process parameter of the second fabrication cluster.

18. The apparatus of claim 16 wherein at least one of the underlying film thickness, critical dimension, and profile of the second patterned structure is used to alter at least one process parameter of the first fabrication cluster.

19. The apparatus of claim 16 wherein at least one of the underlying film thickness, critical dimension, and profile of the first patterned structure is used to alter at least one process parameter of the first fabrication cluster.

20. The apparatus of claim 16 wherein at least one of the underlying film thickness, critical dimension, and profile of the second patterned structure is used to alter at least one process parameter of the second fabrication cluster.

21. The apparatus of claim 16 wherein the metrology data store is configured to store and access pairs of simulated diffraction signals and corresponding sets of profile parameters for the second patterned structure.

22. The apparatus of claim 16 wherein the metrology data store is configured to store and access sets of training data for an optical metrology machine language system and/or a trained optical metrology machine language system for the second patterned structure.

23. The apparatus of claim 16 wherein the metrology processor is configured to receive, process, and transmit metrology data from and to offline or remote metrology data sources.

24. The apparatus of claim 16 wherein the metrology processor is coupled to a process simulator.

25. The apparatus of claim 16 wherein the metrology processor is coupled to a process simulator and the metrology processor is configured to receive and process metrology data from other sources and/or to process and transmit metrology data from the process simulators, including values of profile parameters, material refraction parameters, and metrology device parameters to other fabrication systems.

26. A method of managing metrology data related to structures in a wafer undergoing one or more fabrication processes, the method comprising:
 a) creating an optical metrology model for the patterned structure, the optical metrology model having profile parameters, material refraction parameters, and metrology device parameters;
 b) defining ranges of values for the profile parameters, material refraction parameters, and metrology device parameters;
 c) obtaining one or more measured diffraction signals of the patterned structure;
 d) optimizing the optical metrology model to obtain an optimized optical metrology model using the ranges of values defined in b) and the one or more measured diffraction signals of the patterned structure obtained in c);
 e) for at least one parameter from amongst the material refraction parameters and the metrology device parameters, setting the at least one parameter to a fixed value within the range of values for the at least one parameter;
 f) generating one or more metrology data stores using the optimized optical metrology model, wherein the one or more metrology data stores are used to determine the profile parameters of the patterned structure;
 g) determining the profile parameters of the patterned structure using a measured diffraction signal off the patterned structure and the one or more generated metrology data stores; and
 h) associating the determined patterned structure profile parameters to identifying information related to material data, metrology device data, location of the patterned structure in the wafer, wafer identification, and/or fabrication step identification.

27. The method of claim 26 further comprising:
 i1) storing the associated patterned structure profile parameters and identifying information in a metrology data store.

28. The method of claim 27 further comprising:
 i2) using the patterned structure profile parameters and/or identifying information to modify at least one process variable or modify a setting of a fabrication device in a fabrication cluster in the fabrication system.

29. The method of claim 28 further comprising:
 i3) transmitting the patterned structure profile parameters and/or identifying information to another fabrication system, wherein the profile parameters are used to modify at least one process variable of the another fabrication system.

30. The method of claim 28 wherein the another fabrication system is for a prior fabrication step of the wafer application.

31. The method of claim 30 wherein the another fabrication system is for a later fabrication step of the wafer application.

* * * * *